United States Patent
Underwood et al.

(10) Patent No.: US 8,888,923 B2
(45) Date of Patent: Nov. 18, 2014

(54) COMPONENT, METHOD AND SYSTEM OF SANITISING A WATER PURIFICATION APPARATUS AND/OR A DISTRIBUTION APPARATUS

(75) Inventors: Lee Underwood, High Wycombe (GB); Alan Mortimer, Henley-on-Thames (GB)

(73) Assignee: VWS (UK) Limited, Marlow, Bucks (GB)

( * ) Notice: Subject to any disclaimer, the term of this patent is extended or adjusted under 35 U.S.C. 154(b) by 254 days.

(21) Appl. No.: 13/123,873

(22) PCT Filed: Oct. 14, 2009

(86) PCT No.: PCT/GB2009/051368
§ 371 (c)(1),
(2), (4) Date: Apr. 12, 2011

(87) PCT Pub. No.: WO2010/043897
PCT Pub. Date: Apr. 22, 2010

(65) Prior Publication Data
US 2011/0192429 A1    Aug. 11, 2011

(30) Foreign Application Priority Data
Oct. 16, 2008 (GB) .................. 0818922.7

(51) Int. Cl.
| | |
|---|---|
| *B08B 9/00* | (2006.01) |
| *B08B 9/027* | (2006.01) |
| *C02F 1/00* | (2006.01) |
| *A61L 2/18* | (2006.01) |
| *C02F 1/50* | (2006.01) |
| *C02F 1/28* | (2006.01) |
| *C02F 1/32* | (2006.01) |
| *C02F 1/76* | (2006.01) |

(52) U.S. Cl.
CPC .  *C02F 1/008* (2013.01); *A61L 2/18* (2013.01); *C02F 1/50* (2013.01); *C02F 1/001* (2013.01); *C02F 1/283* (2013.01); *C02F 1/32* (2013.01); *C02F 1/76* (2013.01); *C02F 2201/006* (2013.01); *C02F 2303/04* (2013.01); *C02F 2303/185* (2013.01)
USPC .................... 134/22.13; 123/22.1; 123/22.11; 123/22.17

(58) Field of Classification Search
None
See application file for complete search history.

(56) References Cited

U.S. PATENT DOCUMENTS

| | | | |
|---|---|---|---|
| 3,372,808 A | 3/1968 | Sabo | |
| 4,720,800 A | 1/1988 | Suzuki et al. | |

(Continued)

FOREIGN PATENT DOCUMENTS

| | | |
|---|---|---|
| CN | 2740599 Y2 | 11/2005 |
| DE | 40 28 529 | 3/1992 |

(Continued)

OTHER PUBLICATIONS

English Machine Translation of JP 10-066980.*

(Continued)

*Primary Examiner* — Nicole Blan
(74) *Attorney, Agent, or Firm* — Drinker Biddle & Reath LLP

(57) ABSTRACT

A sanitant component comprising a sanitant to sanitize at least a part of a water purification apparatus and/or a water distribution apparatus and one or more sanitant receivers to receive residual sanitant and/or sanitant products from the water purification apparatus and/or water distribution apparatus. In this way, residual sanitant and/or sanitant products from the water purification apparatus and/or water distribution apparatus can be conveniently collected back into the sanitizing component for easier, and/or quick and/or more convenient disposal.

12 Claims, 4 Drawing Sheets

(56) References Cited

U.S. PATENT DOCUMENTS

| | | | |
|---|---|---|---|
| 4,881,176 A | 11/1989 | Kononov | |
| 4,969,991 A | 11/1990 | Valadez | |
| 5,152,252 A | 10/1992 | Bolton et al. | |
| 5,179,281 A | 1/1993 | Tawil et al. | |
| 5,192,424 A | 3/1993 | Beyne et al. | |
| 5,276,432 A | 1/1994 | Travis | |
| 5,294,916 A | 3/1994 | Bolton et al. | |
| 5,296,655 A | 3/1994 | Sargent et al. | |
| 5,328,597 A | 7/1994 | Boldt, Jr. et al. | |
| 5,354,979 A | 10/1994 | Adelson et al. | |
| 5,512,178 A * | 4/1996 | Dempo | 210/638 |
| 5,526,841 A | 6/1996 | Detsch et al. | |
| 5,925,240 A | 7/1999 | Wilkins et al. | |
| 6,048,456 A * | 4/2000 | Palmer | 210/282 |
| 6,106,771 A | 8/2000 | Fitton | |
| 6,139,731 A * | 10/2000 | Harvey et al. | 210/175 |
| 7,033,509 B2 * | 4/2006 | Klein et al. | 210/753 |
| 2003/0196959 A1 * | 10/2003 | Hughes | 210/669 |
| 2004/0084382 A1 * | 5/2004 | Ryazanova et al. | 210/748 |
| 2004/0140267 A1 * | 7/2004 | Schiltz | 210/663 |
| 2005/0109704 A1 * | 5/2005 | Doxey et al. | 210/739 |
| 2005/0115877 A1 * | 6/2005 | Underwood et al. | 210/143 |
| 2006/0027463 A1 | 2/2006 | Lavelle et al. | |
| 2008/0034846 A1 * | 2/2008 | Mortimer et al. | 73/61.41 |

FOREIGN PATENT DOCUMENTS

| | | | |
|---|---|---|---|
| JP | 61025688 A2 | | 2/1986 |
| JP | 10066980 A | * | 3/1998 |
| WO | WO 02/38069 | | 5/2002 |
| WO | WO 0238069 A1 | * | 5/2002 |
| WO | WO 03/076321 | | 9/2003 |
| WO | WO 03/076342 | | 9/2003 |
| WO | WO 2006/018606 | | 2/2006 |

OTHER PUBLICATIONS

International Preliminary Report on Patentability and Written Opinion, dated Apr. 28, 2011, 7 pages.
International Search Report, dated Jan. 18, 2010.
The State Intellectual Property Office of the People's Republic of China, First Office Action, dated Oct. 10, 2012, for Application No. 200980140289.4, 6 pages.
Examination Report From Japanese Patent and Trademark Office, Application P2011-531567, dated Mar. 12, 2013, Notice of Reasons for Rejection, 7 pages.

* cited by examiner

COMPONENT, METHOD AND SYSTEM OF SANITISING A WATER PURIFICATION APPARATUS AND/OR A DISTRIBUTION APPARATUS

FIELD OF THE INVENTION

The present invention relates to a component, method and system of sanitising a water distribution apparatus and/or a water purification apparatus, particularly but not exclusively for laboratory water. Sanitising includes cleaning and/or disinfection.

BACKGROUND

Water purification apparatus for use in laboratories and healthcare facilities are well known. Generally they involve the reduction and/or removal of contaminants and impurities to very low levels from a water source, as well as any impurities originating from within the apparatus itself. They typically contain a variety of technologies that remove particles, bacteria, ionic species and organic substances and/or molecules.

One very important parameter for many purified water applications is that the bacteria levels are less than prescribed limits. As well as limits on viable bacteria, frequently there are limits on bacterial by-products such as endotoxins, RNase, DNase, alkaline phosphatase, etc., as each of these impurities can have detrimental effects on specific analysis or research.

Micro-organisms, including bacteria and their by-products, are routinely removed from high purity water by a number of techniques, including, but not limited to, reverse osmosis, micro-filtration, ultrafiltration, adsorption and UV irradiation. Despite this array of technologies, and maintaining active recirculation of the purified water, micro-organisms can, under some situations, still develop within the water purification apparatus, and in extreme cases can form biofilms on the surface of components, tubing, pumps etc., leading to contamination of the highly purified water and in some cases leading to a requirement to replace the components themselves.

Regular sanitisation of water purification apparatus is therefore required to ensure optimum performance of the apparatus, and to reduce and hopefully eliminate any contaminants in the water purification apparatus, such as bacteria or micro-organisms adhearing to a surface therein.

Sanitisation of water purification apparatus is conventionally carried out by taking the apparatus 'off line', followed by the addition of hazardous chemicals which are generally circulated for a set period within the apparatus to ensure all micro-organisms are destroyed, before being rinsed or flushed out of the apparatus. Naturally, it is important that all the chemicals are removed prior to return of the apparatus to normal usage, as cleaning chemicals are generally damaging or otherwise dangerous to the activities that the purified water is being applied to.

Whilst cleaning chemicals can be added manually, it is preferred for them to be added from a dedicated container able to ensure the correct introduction, supply and dosage of the chemical or substance. Our WO 03/076321 A1 shows a separable component adapted to sanitise and/or clean one or more parts of a host water treatment apparatus. The component is adapted to properly co-operate with the host apparatus, to ensure the correct introduction and supply of the sanitant in the component into the host apparatus.

However, all known sanitising systems and apparatus still require the rinsing and flushing out of the chemicals and residues from the water purification apparatus through an outlet and passed to a drain or to a waste receptacle. These are flushed out by a stream or a series of streams of fresh water, all of which also goes to the drain or to the waste receptacle. Naturally, it is desired to ensure the removal of the cleaning chemicals and residues to the greatest extent, such that significant volumes of water are required, especially to flush away the last remaining fractions of the cleaning chemicals and residues.

Waste receptacles are required where the chemicals and residues are not allowed to be passed to a drain due to local or site limitations, also requiring separate off-site disposal. This off-site disposal increases the complication and cost of the sanitisation process.

Moreover, the rinsing and flushing out of the chemicals from the water purification apparatus also takes some time to carry out, adding to the expensive downtime for the apparatus until it is able to be operational again.

Purified water provided by a water purification apparatus can be dispensed directly from the apparatus, or be supplied to a water distribution apparatus such as a ring main for dispense in one or more, usually separate, locations. Such water distribution apparatus also require regular sanitisation as described above for water purification apparatus, as they suffer the same or similar problems as described above.

SUMMARY OF THE INVENTION

It is an object of the present invention to provide a component and a simpler system and method for sanitising or cleaning a water purification apparatus and/or a water distribution apparatus.

Thus, according to one aspect of the present invention, there is provided a sanitant component comprising a sanitant to sanitise at least a part of a water purification apparatus and/or a water distribution apparatus and one or more sanitant receivers to receive residual sanitant and/or sanitant products from the water purification apparatus and/or water distribution apparatus.

In this way, residual sanitant and/or sanitant products from the water purification apparatus and/or water distribution apparatus (hereinafter "water purification/distribution apparatus") can be conveniently collected back into the sanitising component for easier, and/or quick and/or more convenient disposal. This may be the sole purpose of the component, or be part of the purpose of the component. The component may be used in addition to the existing pipe work and components of the water purification/distribution apparatus, or may be in the place of one or more sections of pipe work and components of the water purification/distribution apparatus.

Collecting the residual sanitant and/or sanitant products in the sanitising component also reduces, or even removes, the requirement to rinse or flush out the residual sanitant and/or sanitant products from the water purification/distribution apparatus down a drain, etc. thus reducing water wastage, potentially wastage of valuable purified water, during the sanitisation process. Both this and the reduction or elimination of the time to undertake such flushing provides operational and financial as well as environmental advantages. Such time can be reduced from the present 1 hour typically required, to 30 minutes, preferably less than 15 minutes, including some post-sanitising 'safety time'.

After receiving the residual sanitant and/or sanitant products, the sanitant component may wholly or partly neutralise the residual sanitant and/or sanitant products therein. It may also allow removal of the residual sanitant and/or sanitant products from the water purification/distribution apparatus for disposal at another location.

The term "sanitising" as used herein includes cleaning and/or disinfecting. Suitable sanitants therefor are well known in the art, and include peroxides, sulphur-based compounds such as sulphates and sulphites, chlorines and chlorine- or chloride-releasing compounds and substances such as chlorine dioxide, etc, alkalis, acids, aldehydes, detergents, ionic agents and enzymic agents.

The term "residual sanitant" as used herein refers to any sanitant provided by the sanitant component, and remaining in the same form throughout its passage through the water purification/distribution apparatus, generally between an outlet and an inlet of the sanitant component. This can include sanitant carrier material(s).

The term "sanitant products" as used herein refers to one or more of the group comprising: spent sanitant, sanitant compounds, sanitant chemical moieties, sanitant reaction products, sanitant by-products, sanitant residues, sanitised substances, inorganic compounds and substances, sanitised radicals, sanitised residues, and sanitant-affected molecules and compounds.

The sanitant in the sanitant component could be any suitable single or combination of substances and/or chemicals, able to provide a sanitising action on or in at least part of the water purification/distribution apparatus, preferably at least the majority of the water purification/distribution apparatus, and more preferably at least including the lines, pipe work or tubing, pump, oxidisers and filters within a recirculation loop, potentially including any reservoir. One example sanitant is the Elgalite CT3 chlorine tablet available from VWS (UK) Ltd, High Wycombe, UK, comprising >50% Sodium salt chloroisocyanurate and >20% Adipic acid.

The sanitant may include one or more enhancers or tracers, either inherently and/or as an added substance, to assist monitoring of its concentration or level over time, particularly where the sanitant may be non-conductive.

The sanitant may be held as such within the sanitant component ready for use, or it may be generated in the sanitant component prior to use, optionally immediately prior to use, by various processes known in the art, such as wetting or the use of electricity, or the reaction of two or more precursor-compounds or components.

Preferably, the sanitant is or includes an anti-microbial agent.

The sanitant component may be in the form of a replaceable unit or consumable, such as a cartridge.

Preferably, the sanitant component includes a sanitant source, which source may comprise one or more locations, containers, compartments, units or items, housed in the sanitant component, and adapted to release the sanitant either upon conjoining of the sanitant component with the water purification/distribution apparatus, or upon one or more activation controls.

The sanitant component may also comprise one or more locations, containers, compartments, units or items for the sanitant receiver(s). Where the sanitant component comprises two or more different sanitant receivers, two or more of such sanitant receivers may be housed in one or more common locations, etc, or may each be housed individually, or any combination of same.

The sanitant component may also include one or more sanitant receivers selected from the group comprising: adsorbents, absorbents, membranes, filters, neutralisers, catalysts, resins, optionally contained by and/or in a supportive medium or supportive media.

In one particular embodiment of the present invention, the sanitant component includes one or more activated carbon collectors, for example as supplied by PICA of Vierzon, France.

In another embodiment of the present invention, the sanitant component includes one or more resins as an inorganic collector. In another particular embodiment of the present invention, the sanitant component includes activated carbon, ion exchange resins, or mixtures of these, to remove any material carrying the sanitant ('sanitant carrier material') as well as sanitant 'active' material.

In yet another particular embodiment of the present invention, the sanitant component includes the use of ultra-violet light, such as at 185 nanometers to break down the sanitant, followed by the use of ion exchange resin to remove the breakdown products.

A water purification apparatus for the present invention may comprise any number of water purification components, as well as other devices, parts, lines, etc, including but not limited to one or more of the following: pumps, meters, oxidisers, de-ionisers, sensors, valves, drains, controllers, control units, control mechanisms, taps, reservoirs, recirculation loops, filters and membranes. One or more of such components may be integral with the water purification apparatus, such as a pump, and one or more of such components may be separable from the water purification apparatus, such as an ion-exchange cartridge.

Water purification apparatus are known in the art, and are generally intended to provide purified water, preferably as a purified water stream, having a conductivity of less than 1 $\mu$S/cm, preferably less than 0.1 $\mu$S/cm, more preferably less than 0.067 $\mu$S/cm, at 25° C. This can be equated to the purified water stream having a resistivity of at least 1 M$\Omega$-cm, preferably at least 10 M$\Omega$-cm, more preferably at least 15 M$\Omega$-cm. Additionally, purity specifications can be made for organic species to content levels of less than 500 ppb of total organic carbon (TOC), preferably less than 50 ppb; bacteria to levels less than 100 colony forming units (cfu) per milliliter, preferably less than 1 cfu/ml; and for dissolved oxygen and/or particles.

Such water purification apparatus generally only provide up to 1000 liters of purified water per hour, such as up to 5 l/min.

Such water purification apparatus are generally 'stand alone' units, generally only requiring connection to nearby water and electricity supplies to be operable. Thus, they are generally independent and/or moveable units operating in or at a specific location such as a laboratory. Preferably, at least the majority of the purification actions or processes occur within a housing. They are intended to provide a purified water stream only, such stream not being in combination with any other substance or compound.

In general, a water purification apparatus includes an inlet, a pump, one or more de-ionisers, optionally one or more oxidisers, and a water outlet (for dispense of the purified water).

One common oxidiser involves the use of ultraviolet light, and the ultraviolet treatment of water for decomposing organic compounds or substances in water is well known in the art. Apparatus and instruments for providing suitable ultraviolet light are well known in the art, and typically involve emitting ultraviolet light at one or more specific wavelengths in an area or space through which the water passes. The or each oxidiser can be provided as a distinct component, typically a separable component such as a replaceable cartridge, having an ultraviolet emitter therein around which the water stream passes from an inlet to an outlet. The purification of water in the present invention may involve one or more oxidisers, being in series, parallel or both.

Ionic species in the feed water (and any created by any oxidiser(s)) are generally removed from the water stream to provide purified water by the use of one or more de-ionisers. Many types and forms of de-ioniser are known in the art, and include, but are not limited to, one or more of the following; (electro)deionisation apparatus or units, reverse osmosis (RO) units or apparatus, membranes, filters, ion exchange resins and zeolites. The action and operation of de-ionisers is well known in the art, and they are not further described in detail herein.

The water purification apparatus may comprise a plurality of ion-exchangers, including one or more "pre-treatment" ion exchangers upstream of any oxidiser, as well as one or more ion-exchangers downstream of any oxidiser.

A water distribution apparatus for the present invention may comprise any number of purified water distribution components, as well as other devices, parts, lines, etc, including but not limited to one or more of the following: pumps, controllers, meters, (additional or supplementary) oxidisers and/or de-ionisers, valves, drains, control units and mechanisms, taps, filters, membranes.

The purified water provided by the water distribution apparatus may be as hereinbefore defined, and is created by the reduction and/or removal of any or one or more of the contaminants and impurities in a supply water stream. Such purified water can be supplied by one or more water purification components hereinbefore defined, optionally in a nearby or remote location, and optionally in a separate and/or independent apparatus, unit or housing such as the water purification apparatus herein defined.

Such water distribution apparatus are generally units connected to a water purification apparatus to distribute the purified water stream provided therefrom to one or more separate, usually remote, locations. Thus, they are generally independent and/or moveable units having one or more water dispense points. They are intended to provide a purified water stream within a laboratory or a suite of laboratories only, such stream not being in combination with any other substance or compound.

In general, a water distribution apparatus includes a pump, a ring main and one or more water outlets (for dispense of the purified water).

Where the water purification apparatus and water distribution apparatus are connected, the sanitant component could be adapted to sanitise both such apparatus.

The dispense of at least a portion of the purified water from the water purification/distribution apparatus can be provided through any form or type of outlet or outlets, optionally being co-ordinated or separate.

The water purification/distribution apparatus may have a dispense mode or other such form of operation, and a recirculation mode. Preferably, the or each point of dispense of the purified water involves at least one valve, more preferably operable between a dispense position and a recirculating position. One or more valves may also provide control over the volume and/or rate of flow of the purified water at the dispense.

The movement of water through a water purification/distribution apparatus is generally provided by the use of one of more pumps known in the art, and the nature and operation of a pump is not further discussed in detail herein.

Optionally, the sanitant component may be connectable to or at two or more locations, usually ports, in or on the water purification/distribution apparatus, for effecting embodiments of the present invention. For example, for a water purification/distribution apparatus without recirculation, the sanitant component may act in two parts; the first part incorporating the introduction of the sanitant by the sanitant component connected at an upstream location, and a second part incorporating the receiving, preferably including removal or neutralising, of residual sanitant and/or sanitant products at a downstream location. Two connecting locations may also be used with re-circulating systems at any parts thereof.

The parameters for the nature and passage of the sanitant in and through the water purification/distribution apparatus can be dependent upon the nature of the water purification/distribution apparatus, or at least that part of the water purification/distribution apparatus that is to be sanitised, as well as the intended sanitisation programme. Parameters for the nature and process of sanitising at least a portion on a water purification/distribution apparatus are known in the art, and can include variations in concentrations, flow rates, and contact times, which are preferably adjusted to optimise the desired sanitisation programme. This can include one or more flow-stop/start operations, in order to ensure that the sanitant has a stationery period in one or more parts of the water purification/distribution apparatus requiring particular attention.

The sanitant/sanitising products may require more than one pass through the sanitant component for their complete removal from the water purification/distribution apparatus.

In another embodiment of the present invention, the sanitant component is reusable, by being able to be cleaned of collected residual sanitant and/or sanitant products, and recharged with sanitant.

Preferably, the sanitant component has an electronic circuit adapted to cooperate with an electronic circuit in the water purification/distribution apparatus, and cooperation of the sanitant component circuit and the electronic circuit in the water purification/distribution apparatus is only possible when the component is conjoined with the apparatus. The co-operation may be one way, either from component to apparatus or vice versa, or two-way.

The component circuit and the apparatus circuit could communicate via radio, infrared, or any other transmittable waveforms including optical and magnetic contact. Preferably, the circuits communicate by physical electrical contact for maximum robustness of connection, and to minimise interference by other means of communication. Preferably co-operation of the circuits is only possible when the communication is correctly created, and this is only achieved when the sanitant component is correctly installed and/or fitted with the water purification/distribution apparatus.

Each electronic circuit preferably includes a memory capacity and a capability to read/interrogate the other electrical circuit. The electrical circuit in the apparatus preferably includes a central processor, and the electrical circuit in the sanitant component preferably includes or is a data chip or tag, e.g. a microchip such as well known in the art. The electronic circuit of the sanitant component is preferably integral with the component, and more preferably, is formed integrally with the sanitant component during the component manufacture. The electronic circuit is preferably embedded into or mounted onto the sanitant component.

According to a further embodiment of the present invention, the electronic circuit of the sanitant component provides an enablement signal to the electronic circuit of the water purification/distribution apparatus, and/or vice versa.

The enablement signal may include means for the sanitant component or the water purification/distribution apparatus to control the other part.

Information that can be communicated between the electronic circuits of the sanitant component and the water purification/distribution apparatus could include validation information and sanitising processing information. Such information in the sanitant component could be accessed from the component and be displayed by the apparatus.

In typical operation, the electronic circuit of the sanitant component includes at least a data tag, and the presence of the data tag is identified by the electronic circuit of the water purification/distribution apparatus upon correct fitment and/or installation of the sanitant component, which creates a two-way communication protocol. The apparatus can then upload relevant data from the data tag, etc. and the component's circuit can download the relevant information from the apparatus.

In another embodiment of the present invention, lack of co-operation between the electronic circuit of the sanitant component and electronic circuit of the water purification/distribution apparatus indicates the incorrect fitment and/or installation of the component with the apparatus, or incorrect location of a component on the apparatus where more than one location is possible. In another embodiment of the present invention, the lack of co-operation between the electronic circuit of the component and the electronic circuit of the apparatus identifies incorrect operation of the component and/or apparatus, e.g. a sanitant leak.

According to another aspect of the present invention, there is provided a method of sanitising a water purification/distribution apparatus comprising at least the steps of:
(a) conjoining a sanitant component with the water purification/distribution apparatus;
(b) allowing sanitant in the sanitant component to pass into the water purification/distribution apparatus; and
(c) receiving residual sanitant and/or sanitant products from the water purification/distribution apparatus in the sanitant component.

According to another aspect of the present invention, there is provided a system comprising a water purification/distribution apparatus and a separable sanitising component, said component comprising a sanitant to sanitise at least a part of a water purification/distribution apparatus and one or more sanitant receivers to receive residual sanitant and/or sanitant products from the water purification apparatus/distribution apparatus.

Preferably, the water purification/distribution apparatus and the sanitant component are as hereinbefore defined.

The water purification/distribution apparatus acts as a 'host' to the sanitant component in a manner well known in the art, especially where the sanitant component is a separable component such as a separable cartridge, optionally adapted to fit the port for one or more other separable cartridges of the water purification/distribution apparatus such as an ion-exchange or UV cartridge.

In one embodiment of the present invention, the system includes an automated method and/or apparatus for determining the partial or full sanitising of the water purification/distribution apparatus to which a substance has been added, comprising at least the steps of:
(a) conducting one or more measurements of a property of the or an added substance;
(b) comparing the property measurement(s) from step (a) with at least one reference value for that property; and
(c) determining when the comparison in step (b) is within, above or below a pre-determined level for that property.

The substance may be the sanitant or a component of the sanitant, or a separate tracer compound. The substance can have a property such as conductivity, pH, or ionic concentration, which is able to be measured by one or more measuring means, such as sensors. The substance may include one or more additives adapted either to enhance the ability of the substance to generate a signal or property which is measurable, or to produce a signal or measurement that is different than that of another chemical or substance that may be in the apparatus.

The measuring of the property of the substance may be singular. When a plurality of measurements are conducted, they may be periodical, regular, or even continuous. Conducting a series of measurements provides a form of monitoring the substance property.

The reference value or values are generally standard or pre-determined value or values which could be programmed into a suitable comparator, such as any computer or controller apparatus. Such reference value or values could be determined by prior experimentation with the apparatus or equipment, or other routine trial and error measurement operations.

Further embodiments of this automated method and apparatus are described in our WO2006/018606 A1 which is included herein by way of reference.

The present invention encompasses all combinations of various embodiments or aspects of the invention described herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

BRIEF DESCRIPTION OF THE DRAWINGS

Embodiments of the present invention will now be described by way of example only, and with reference to the accompanying drawings in which.

DESCRIPTION OF THE PREFERRED EMBODIMENTS

Figure 1:
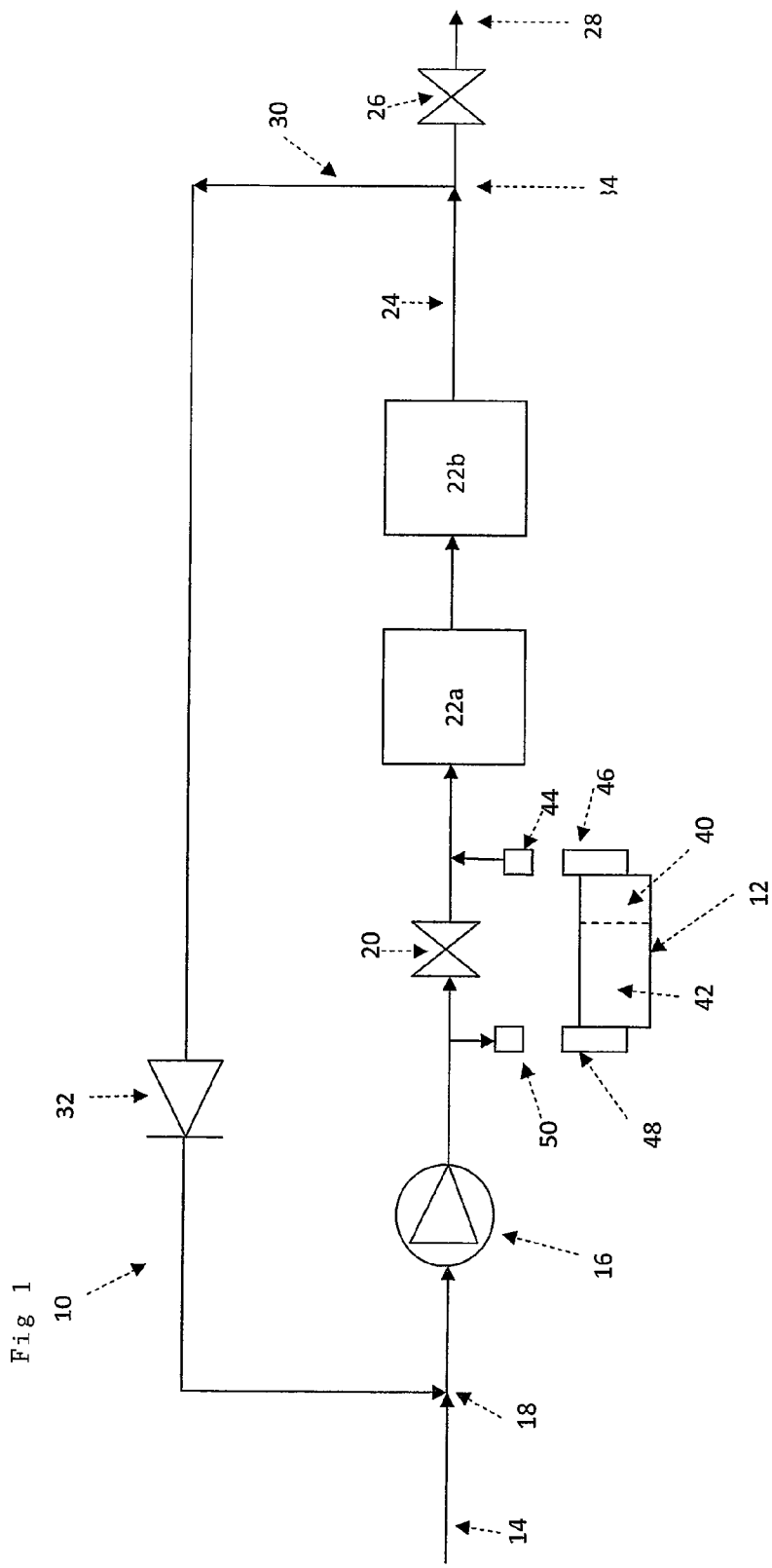
FIG. 1 schematically shows a system according to one embodiment of the present invention.

Referring to the drawings, FIG. 1 shows a system comprising parts of a water purification apparatus 10, and a separable sanitising component 12. Many of the usual or standard parts of a water purification apparatus are not shown in FIG. 1 for clarity and because they are known to the person skilled in the art.

FIG. 1 shows an incoming water stream 14, available from a water source or the like, which passes through a pump 16. From pump 16, the water stream passes through a valve 20 before passing through one or more water purification components. FIG. 1 shows, by way of example only, two water purification components 22a, 22b, which could comprise an oxidiser such as an ultraviolet light emitter, followed by an ion-exchanger, adapted to remove the ionic species in the feed water as well as those created by the oxidiser; and so to purify the water stream. The so-formed purified water stream 24 passes through a second valve 26 to be provided as dispensed purified water 28, by any outlet known in the art.

FIG. 1 also shows a recirculation loop 30 extending from a first tee piece 34 located before the second valve 26, the recirculation passing through a one way valve 32, (which valve 32 also provides the dispense pressure), to a second tee piece 18. Recirculation loops are well known in the art, and commonly provide maintenance of the purity of the purified water stream 24 during periods of non-dispense from the water purification apparatus 10 operating continuously or intermittently.

The sanitising component 12 shown in FIG. 1 comprises a cartridge, having at least two locations therein, figuratively shown in the embodiment of FIG. 1 as a first location 40 and a second location 42. The two locations 40, 42 may together occupy a part or all of the volume of the sanitising component 12, and may comprise the same or different volumes. They may be side-by-side or above-and-below, or any other suitable configuration.

The sanitant component 12 also comprises an outlet 46 and an inlet 48. The first location 40 includes a sanitant source, generally being a tablet or pocket of sanitant at or near the outlet 46, which is able to provide sanitant through the outlet 46 upon conjoining of the sanitising component 12 with a first co-operating port 44 of the water purification apparatus 10. The sanitising component inlet 48 is also able to conjoin with a corresponding second port 50 of the water purification apparatus 10.

The first and second ports 44, 50 of the water purification apparatus 10 may be specifically adapted to conjoin with a sanitising component, or may be ports otherwise used for conjoining with one or more other components such as a water treatment component such as an ion-exchange cartridge known in the art. Thus, the shape, size and design of the sanitising component 12 may be the same or sufficiently similar, at least at its outlet 46 and inlet 48, to other components adapted for use with the water purification apparatus 10 in this way.

Preferably, the sanitising component 12 is able to be hosted in the water purification apparatus 10 by interchanging it with an existing water treatment component, and to be useable in the same receiving part of the water treatment apparatus 10. The second location 42 of the sanitising component 12 includes one or more sanitant receivers such as activated carbon, membranes, filters or pads, through which water provided through the sanitising component inlet 48 passes.

In use, when the water purification apparatus 10 requires at least partial or full cleaning, disinfecting or sanitisation, the sanitising component 12 is conjoined with the water purification apparatus 10 (optionally in the place of an ion-exchange cartridge), and sanitant from the sanitant source in the first location 40 is provided through the outlet 46 of the sanitising component 12 and the first port 44 and into the water purification apparatus 10, generally upstream of one or more of the water purification components such as components 22a and 22b shown in FIG. 1. Sanitant passes through the components 22a, 22b and around the recirculation loop 30, and with closing of the first valve 20, residual sanitant and/or sanitant products in the water stream pass through the second port 50 and the inlet port 48 of the sanitant component 12 and through the one or more receivers in the second location 42, so as to be collected and optionally partly or fully neutralised thereby. Water can then pass through the sanitising component 12 and back out through the outlet 46 of the sanitising component 12. Water still circulates through the sanitant component and out through the outlet 46.

In this way, residual sanitant and/or sanitant products passing around the water purification apparatus 10 can be received and collected back into the sanitising component 12, whilst water continues to circulate around the water purification apparatus 10. This avoids the need for significant new volumes of water where conventionally residual sanitant and/or sanitant components were rinsed or flushed out directly to a drain either through outlet 28 or through an extra valve and drain in the recirculation loop 30.

Moreover, by the direct collection of the sanitant and/or sanitant products by an activated collector, less time is required to reduce and/or remove the level of residual sanitant in the water purification apparatus to an acceptable low level, allowing the water purification apparatus to be put back on line for purification operation in less time.

When the sanitising component 12 has collected residual sanitant and/or sanitant products, it can be disjoined from the water purification apparatus 10 either for disposable, or for its own cleaning and re-use, generally by reactivation of the sanitant source and sanitant receiver. The water purification apparatus 10 can be returned to its normal operation either by removal of the sanitising component 12 (and optional replacement of any prior-removed cartridge), or by action of the first valve 20.

Figure 2:
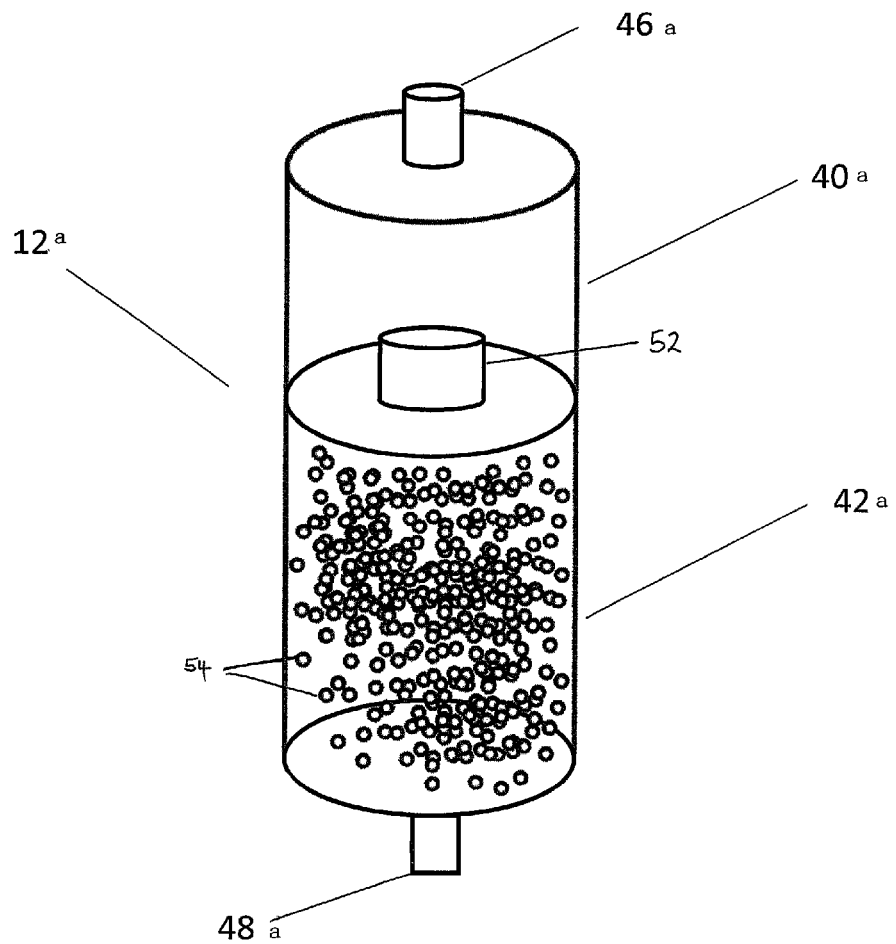
FIG. 2 shows a perspective view of a first sanitant component according to another embodiment of the present invention.

FIG. 2 shows a perspective view of a first sanitising component 12a being suitable for use as the sanitising component in the system of FIG. 1.

The first sanitising component 12a of FIG. 2 is shown as a rounded cartridge. The first location 40a of the sanitising component 12a includes a chlorine tablet 52 as the sanitant source, able to dissolve with a flow of water and pass when required through the outlet 46a and the first cooperating port 44 of the water purification apparatus 10. The second location 42a of the first sanitising component 12a includes activated carbon, shown as representative particles or beads 54 in FIG. 2. The flow of water enters the first sanitising component 12a through an inlet 48a which can connect to the second co-operating port 50 of the water purification apparatus 10. Generally, there is a suitable divider between the first and second locations 40a, 42a, such as a mesh or sintered polypropylene sheet.

The sanitising component cartridge shown in FIG. 2 could be several centimeters to 1 m or more in length, and several centimeters in diameter, usually having the same or similar dimensions to conventional water purification cartridges known in the art. Alternatively, the first and second locations 40a, 42a could lie next to each other with suitable through-porting thereinbetween.

Figure 3:
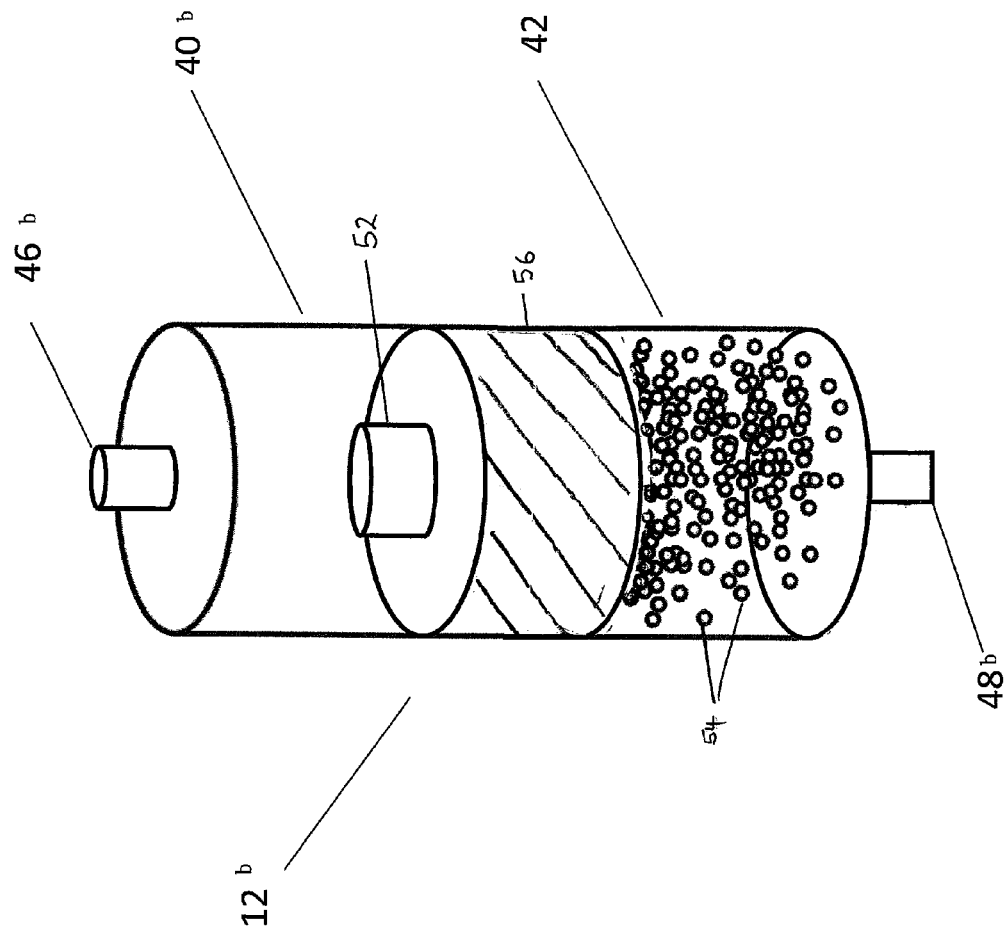
FIG. 3 shows a perspective view of a second sanitant component according to another embodiment of the present invention.

FIG. 3 shows a perspective view of a second sanitising component 12b also being suitable for use as the sanitising component in the system of FIG. 1.

The second sanitising component 12b of FIG. 3 has a similar first location 40b to that of the first sanitising component 40a for a chlorine tablet 52 as the sanitant source, able to dissolve with a flow of water and pass when required through the outlet 46b and the first co-operating port 44 of the water purification apparatus 10. A second location 42b of the second sanitising component 12b includes activated carbon, shown as representative particles or beads 54 in FIG. 3. The flow of water enters the second sanitising component 12b through an inlet 48b which can connect to the second co-operating port 50 of the water purification apparatus 10. Between the first and second locations 40b, 42b is a third location 56, being a second compartment for the sanitant receiver, and including one or more resins to particular receive inorganic substances and compounds in the water passing through the second sanitising component 12b, such as residual sanitant carrier material. Optionally, one or more such resins are admixed in the second location 42a of the first sanitising component 12a.

The present invention provides a system, method and component able to provide a number of advantages, including but not limited to one or more of the following.

Firstly, there is reduced system complexity as no valves and/or pipe work to a drain are required.

Secondly, there is a reduction in the time required for the post-sanitisation rinsing of the water purification apparatus, such that the water purification apparatus requires less time off line, providing operational and financial advantages.

Thirdly, there is a significant reduction in the water usage required to rinse and flush out the sanitant. In particular, there is a significant environmental advantage due to the reduced rinse water requirement, which would otherwise be directed down the drain. Indeed, in some locations, passing spent sanitisation chemicals to a drain may be prohibited, and the present invention enables compliance with such local requirements.

Fourthly, there is safer containment of residual sanitant and/or sanitant products. Such sanitant and products can, and generally are, hazardous, not only to water purification apparatus, but sometimes to the environment in general. The present invention provides for their safe containment, and thus safer disposal or neutralisation, rather than their passage down a drain. This therefore also reduces or eliminates environmental contamination that may occur thereby.

EXAMPLE 1

Test details: A 476 ml sanitisation pack was divided into 3 sections, the first containing 270 ml of granular activated carbon as available from Kureha Corp (Japan), the second containing 150 ml of Dowex MR-450 UPW mixed bed resin as available from Dow Corp (USA) and the third containing a CT3 chlorine release tablet from VWS (UK) Limited.

Figure 4A:
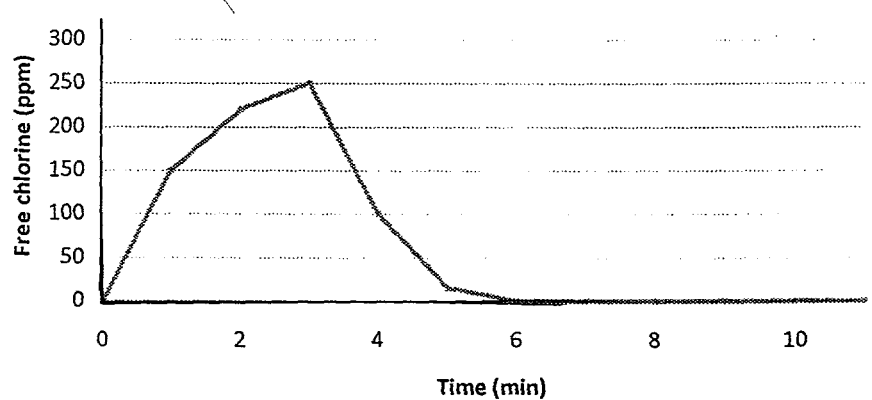
FIGS. 4a and 4b are graphs of the chlorine removal and conductivity change respectively over time for Example 1 of the present invention.
Figure 4B:
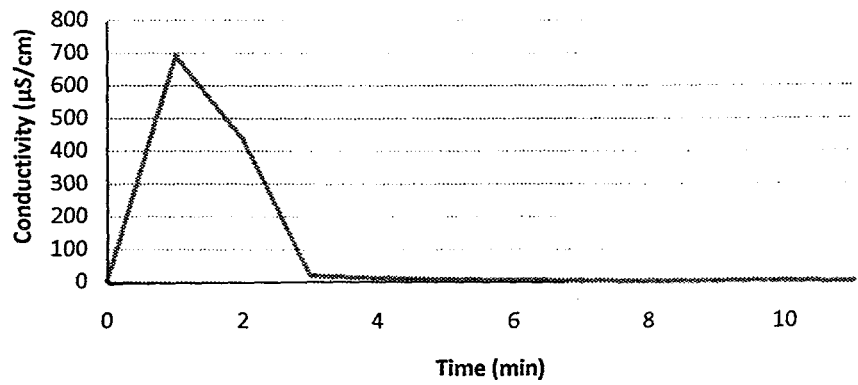

600 ml of ultrapure water was recirculated from a vessel by a pump through the sanitisation pack, a conductivity measuring in-line cell and back to the vessel at a flow rate of 0.5 l/min. Regular samples for free chlorine were taken, and the conductivity regularly recorded, for 11 minutes. The results are shown in the graphs of FIGS. 4a and 4b herewith Graph 4a shows it took 7 minutes to remove any free chlorine from the system. This compares with typical conventional sanitisation cycles of around 1 hour. Running the method of the present invention for a further few minutes, such as up to 10 or 15 minutes to allow some margin of error and/or safety purposes, still means that the method of the present invention is four times faster than a typical conventional sanitisation cycle.

Graph 4b shows that the conductivity of the water in the sanitisation pack fell to near zero after only 5 minutes, and was zero (as a de minimus figure) after 7 minutes, providing confirmation of the data and effect of the results in the graph of FIG. 4a.

It will be appreciated that although specific embodiments of the invention have been described herein for the purposes of illustration, various modifications may be made without deviating from the spirit of the scope of the invention.

The invention claimed is:

1. A method of sanitising a water purification/distribution apparatus comprising at least the steps of:
conjoining a sanitant cartridge with the water purification/distribution apparatus, the sanitant cartridge containing at least a water inlet, a first compartment containing a solid chlorine based sanitant, a second compartment containing an activated carbon absorbent, and a water outlet;
passing water from the water purification/distribution apparatus through the sanitant cartridge to allow sanitant from the first compartment of the sanitant cartridge to pass into the water purification/distribution apparatus;
returning water from the water purification/distribution apparatus to the sanitant cartridge;
receiving, collecting and retaining residual sanitant and/or sanitant products from the water returned to the sanitant cartridge by absorption into the activated carbon in the second compartment; and
removing the sanitant cartridge from the water purification/distribution apparatus so as to permit normal operation of the water purification/distribution apparatus.

2. A method as claimed in claim 1 further comprising the step of completing the sanitising of the water purification/distribution apparatus in less than 30 minutes.

3. A method as claimed in claim 1 further comprising the step of circulating water containing the sanitant through the at least part of the water purification/distribution apparatus and back to the cartridge and into the second portion of the cartridge for collection and retention.

4. A method as claimed in claim 1 wherein the second compartment of the sanitant cartridge includes ion exchange resin.

5. A method as claimed in claim 1 wherein the sanitant cartridge is reusable.

6. A method as claimed in claim 1 wherein the sanitant is or includes an anti-microbial agent.

7. A method as claimed in claim 1 wherein the sanitant cartridge includes an electronic circuit that cooperates with an electronic circuit in the water purification/distribution apparatus when the cartridge is conjoined with the water purification/distribution apparatus.

8. A method as claimed in claim 1 wherein the cartridge includes a data tag.

9. A method as claimed in claim 1 wherein the cartridge is reusable and the method further comprises the step of cleaning the second compartment of the cartridge and reloading of the sanitant.

10. A method as claimed in claim 1 further comprising the step of allowing the sanitant to pass through all the components of the water purification/distribution apparatus prior to returning to the sanitant cartridge.

11. A method as claimed in claim 1 further comprising the step of steps:
removing a purification component of the water purification/distribution apparatus; and
inserting the sanitant cartridge into the water purification/distribution apparatus in the location of the removed component.

12. A method as claimed in claim 1 wherein the step of passing water from the water purification/distribution apparatus through the sanitant cartridge to allow sanitant from the first compartment of the sanitant cartridge to pass into the water purification/distribution apparatus is accomplished by circulating water through the water purification/distribution apparatus without use of a separate pump in the sanitant cartridge.

* * * * *